United States Patent
Yokota et al.

(10) Patent No.: US 6,357,454 B1
(45) Date of Patent: Mar. 19, 2002

(54) METHOD FOR WASHING AND STERILIZING BEER SUPPLY PIPE

(75) Inventors: Kenichi Yokota, Shiga; Masayoshi Matsushima, Kyoto, both of (JP)

(73) Assignee: Jyonan Electric Industrial Co., Ltd., Uji (JP)

( * ) Notice: Subject to any disclaimer, the term of this patent is extended or adjusted under 35 U.S.C. 154(b) by 0 days.

(21) Appl. No.: 09/433,303

(22) Filed: Nov. 3, 1999

(51) Int. Cl.[7] ................................................ B08B 9/00
(52) U.S. Cl. .......................... 134/22.12; 134/2; 134/3; 134/22.1; 134/22.11; 134/22.13; 134/22.18; 134/26; 134/36; 134/42; 134/167 R; 134/167 C; 134/168 R; 205/701
(58) Field of Search .............................. 134/2, 3, 22.1, 134/22.11, 22.12, 22.13, 22.18, 26, 36, 42, 167 R, 167 C, 168 R; 205/701, 746

(56) References Cited

U.S. PATENT DOCUMENTS

| | | | |
|---|---|---|---|
| 872,494 A | * 12/1907 | Blackburn | 134/167 C |
| 927,893 A | * 7/1909 | Steiger | 134/167 C |
| 2,016,926 A | * 10/1935 | Josepowitz | 134/167 C |
| 2,022,882 A | * 12/1935 | Erdmann | 134/167 C |
| 2,098,525 A | * 11/1937 | Smith | 134/167 C |
| 2,175,951 A | * 10/1939 | Bolleri | 134/167 R |
| 5,408,991 A | * 4/1995 | Iida et al. | 128/4 |
| 5,593,554 A | * 1/1997 | Yamanaka et al. | 204/252 |
| 5,720,869 A | * 2/1998 | Yamanaka et al. | 205/701 |
| 5,759,489 A | * 6/1998 | Miura et al. | 422/28 |
| 5,944,978 A | * 8/1999 | Okazaki | 205/701 |
| 5,951,859 A | * 9/1999 | Miura et al. | 210/192 |
| 6,106,691 A | * 8/2000 | Nakamura et al. | 205/701 |

FOREIGN PATENT DOCUMENTS

| | | |
|---|---|---|
| EP | 0 605 882 A1 | 7/1994 |
| JP | 10071391 | * 3/1998 |
| JP | 11033553 | * 2/1999 |
| JP | 11 290855 | * 10/1999 |
| WO | WO 95/12543 | 5/1995 |

* cited by examiner

Primary Examiner—Sharidan Carrillo
(74) Attorney, Agent, or Firm—Rader Fishman & Grauer

(57) ABSTRACT

The dregs or other deposits in a beer pipe 10 are washed out by introducing strong alkaline electrolyzed water produced by an electrolyzed functional water generator 1, in which an outlet 71 is connected to the beer pipe 10 as shown in FIG. 2. In the next step, referring to FIG. 3, strong acidic electrolyzed water produced by the water generator 1 is introduced into the beer pipe 10 for exterminating bacteria/microorganisms inside the beer pipe 10. An electrolyte solution containing dissolved electrolytes such as sodium chloride (NaCl) is electrolyzed in the water generator 1. The thus strong alkaline electrolysed water contains a trace of sodium hydroxide (NaOH) and hydroxide ions (OH$^-$), which exhibit a soap-like action and dissolve beer dregs (proteins). The strong acidic electrolyzed water contains hypochlorous acid (HClO), whose bactericidal effect kills all bacteria/microorganisms.

16 Claims, 6 Drawing Sheets

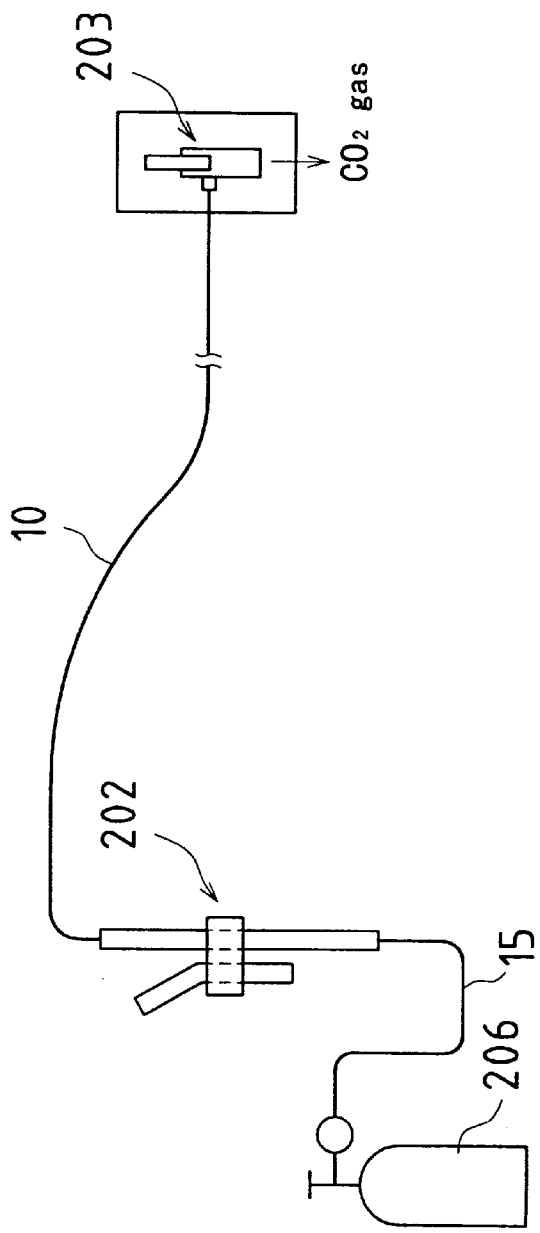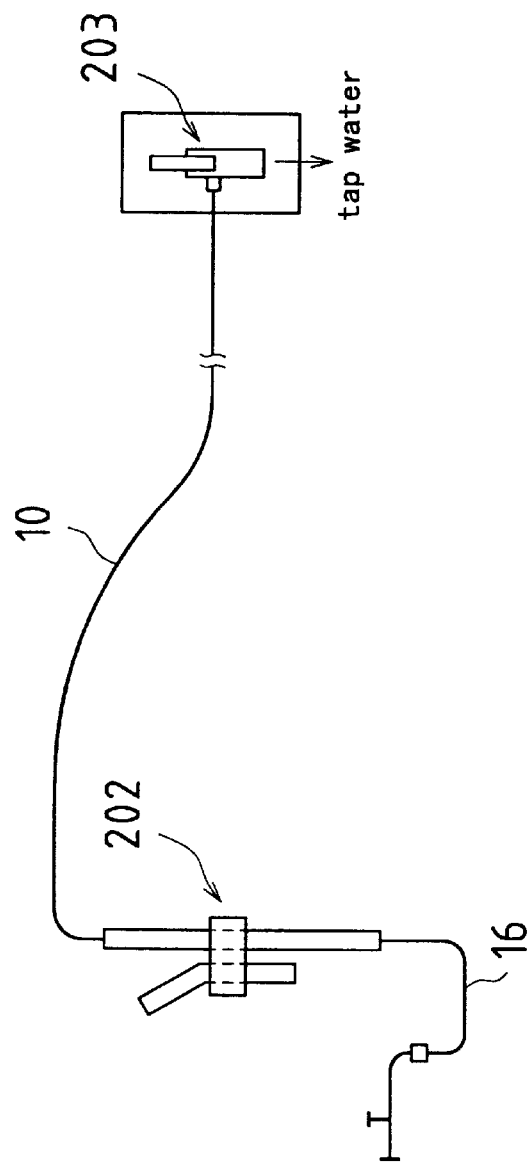

METHOD FOR WASHING AND STERILIZING BEER SUPPLY PIPE

FIELD OF THE INVENTION

The present invention relates to a method for washing and sterilising a beer supply pipe employed in a beer supply system for delivering draught beer in a beer barrel to a beer dispenser tap or a beer pipe of a beer dispenser.

PRIOR ART

FIG. 1 shows a beer supply system for delivering draught beer from a beer barrel to a tap, generally installed in large pubs and beer halls.

In the system of FIG. 1, a refrigerator 200 for cooling draught beer to desired temperatures houses a draught beer barrel 201. An outlet 211 of the beer barrel 201 is equipped with a connector 202 having a $CO_2$ gas inlet 221. A beer dispenser tap 203 is located in the hall or kitchen and connected to the connector 202 on the beer barrel 201 via a beer pipe 10 (e.g. vinyl tube). Further, a $CO_2$ cylinder 204 is connected to the $CO_2$ gas inlet 221 on the connector 202, so that the draught beer stored in the beer barrel 201 is delivered to the tap 203 under the gas pressure. The beer is poured into a mug or the like by operating the tap 203.

For the purpose of simplification, FIG. 1 depicts a single beer pipe extending from a beer barrel. In the actual beer supply system, a row of pipes are allocated on one beer barrel.

Recently, beer dispensers for cooling draught beer to desired temperatures are employed in relatively small-sized restaurants, etc. A typical beer dispenser comprises a cooler, a capillary cooling tube and a beer dispenser tap. Under the gas pressure from a $CO_2$ cylinder, barrelled beer is delivered into the capillary cooling tube, where the beer is cooled.

In the beer pipes for delivering draught beer, the internal wall is contaminated with dregs or lees of beer (mainly consisting of proteins), bacteria/microorganisms, etc. Dregs of beer deteriorate the taste of the beer, and propagation of bacteria and microorganisms is unsanitary. Therefore, the beer pipes require regular cleaning. However, it is impossible to sufficiently wash out the beer dregs composed of a mass of proteins and bacteria/microorganisms, by simply washing the beer pipe with tap water.

Conventionally, cleaning of a beer pipe is conducted while the pubs, etc. are closed. The cleaning operation comprises withdrawing the beer from the beer pipe, filling the pipe with a cleaning material solution (washing solution) mainly comprising caustic soda (sodium hydroxide) or caustic potash (potassium hydroxide) or with a cleaning material solution (washing solution) mainly comprising caustic soda (sodium hydroxide) or caustic potash (potassium hydroxide) and further comprising hypochlorous acid soda (sodium hypochlorite), withdrawing the washing solution from the pipe after a predetermined time (e.g. 15 minutes to 8 hours), and washing the pipe with tap water. The filling and withdrawal of the cleaning solution may be repeated before the washing step. Where the cleaning solution mainly comprises caustic soda or caustic potash but contains no hypochlorous acid soda, sterilisation is effected by introducing an aqueous solution of hypochlorous acid soda (effective chlorine concentration: 200 to 500 ppm) into the pipe, after the pipe is washed with the use of the cleaning solution. The aqueous solution of hypochlorous acid soda has a bactericidal effect. The beer pipe of a beer dispenser is cleaned in a like manner.

However, this cleaning process has some defects due to the cleaning solution whose principal constituents are toxic chemicals such as caustic soda and caustic potash. For one, the washing step must be carried out carefully and completely so as not to leave any caustic soda or other toxic chemicals in the beer pipe, and such washing takes a substantial time.

Besides, the cleaning materials mainly comprising caustic soda, etc. are generally sold in the form of a plate-like or spherical tablet or liquid concentrate. Therefore, the cleaning solution needs to be prepared in a container by dissolving the tablet in water or diluting the liquid concentrate with water. A worker has the risk of hurting himself through physical contact with a highly concentrated toxic solution. Moreover, since the toxic chemicals like caustic soda still remain in the used cleaning solution, the cleaning solution cannot be left untreated. The beer-serving establishments must treat the used cleaning solution and discharge it in sewers on their own, or they need to commission waste treatment specialists for proper disposal.

SUMMARY OF THE INVENTION

It is an object of the present invention to provide a simple and safe method for washing and sterilising a beer supply pipe which delivers draught beer stored in a beer barrel to a beer tap, or a beer pipe of a beer dispenser.

According to the present invention, the method of washing and sterilising a beer supply pipe comprises a washing step of introducing strong alkaline electrolysed water into the beer supply pipe, and a sterilisation step of introducing strong acidic electrolysed water into the beer pipe, wherein both waters are produced by means of an electrolysed functional water generator.

The electrolysed functional water generator employed herein is a known apparatus which comprises an electrolytic cell including an anode, a cathode and a diaphragm provided between these electrodes. The electrolytic cell contains an aqueous electrolyte solution comprised of dissolved electrolytes such as sodium chloride (NaCl). The aqueous electrolyte solution is electrolysed by applying a DC voltage on the anode and the cathode, thereby generating strong alkaline electrolysed water and strong acidic electrolysed water.

This electrolysed functional water generator provides strong alkaline electrolysed water having a hydrogen ion concentration (pH) of 11.0 to 12.5 and an oxidation-reduction potential (ORP) of −650 mV or lower, and strong acidic electrolysed water having a hydrogen ion concentration (pH) of 1.5 to 3.0 and an oxidation-reduction potential (ORP) of +1100 mV or greater and containing hypochlorous acid with an effective chlorine concentration of 10 to 50 ppm. Note that the oxidation-reduction potential represents the oxidation capacity or reduction capacity of the solution.

The beer supply pipe washing/sterilisation method of the present invention ensures simple and effective removal of beer dregs deposited inside the beer pipe as well as extermination of bacteria and microorganisms.

Specifically, the electrolysed functional water generator electrolyses the aqueous electrolyte solution containing dissolved electrolytes such as sodium chloride (NaCl) to give strong alkaline electrolysed water and strong acidic electrolysed water. The former contains a trace of sodium hydroxide (NaOH) and hydroxide ions (OH⁻), which dissolve beer dregs by an action similar to soap. The latter contains a trace of hypochlorous acid (10 to 50 ppm), whose bactericidal effect can exterminate any bacteria or microorganisms.

In the strong alkaline electrolysed water for washing, the NaOH content is so limited that physical contact with the water is harmless to humans.

The hypochlorous acid contained in the strong acidic electrolysed water for sterilisation is decomposed and vanishes after being left in the air for a certain period or instantaneously on contact with an organic substance, thereby to turn the water harmless. In addition, reduction of the strong alkaline washing water can be accelerated by adding the strong acidic water, whereby the waters are neutralised to be as harmless as the pre-electrolysis water. Thus, the strong alkaline electrolysed water and strong acidic water used for washing and sterilisation can be discharged into sewers or the like without any special treatment.

In a preferable embodiment, the strong alkaline electrolysed water and the strong acidic electrolysed water are introduced into the beer pipe immediately after each water is produced in the electrolysed functional water generator. The reasons are given below.

Firstly, with respect to the strong alkaline electrolysed water, the water generated in the electrolysed functional water generator exhibits a higher dissolution property for proteins than caustic soda of the same pH value. This is presumably because of the correlation between the pH value and the oxidation-reduction potential (ORP), which is not greater than −650 mV in the case of the strong alkaline electrolysed water. Nevertheless, the strong alkaline electrolysed water is very unstable and prone to be oxidised (i.e. the absolute value of the ORP tends to decrease) Hence, for efficient dissolution of beer dregs (proteins), it is advantageous to utilise strong alkaline electrolysed water with a greater absolute ORP value, namely, just after it is generated.

Secondly, as mentioned above, the strong acidic electrolysed water generated in the electrolysed functional water generator has a hydrogen ion concentration (pH) of 1.5 to 3.0 and an oxidation-reduction potential (ORP) of +1100 mV or greater, and the water contains bactericidal hypochlorous acid. The combination of these factors enables a high sterilisation effect. As the time passes, however, the absolute ORP value decreases and the concentration of hypochlorous acid drops. Accordingly, for a higher sterilisation effect, it is preferable to use the freshest possible strong acidic electrolysed water.

In the above description, each electrolysed water is introduced directly from the electrolysed functional water generator into the beer pipe. Alternatively, the strong alkaline electrolysed water and the strong acidic electrolysed water may be temporarily reserved in separate tanks, from which either water is supplied into the beer pipe.

Specific modes of the washing/sterilisation treatment include a method comprising flowing strong alkaline or strong acidic electrolysed water through the beer pipe at a predetermined rate (e.g. 1.0 to 2.0 l/min), and a method comprising the steps of filling strong alkaline electrolysed water into the beer pipe, withdrawing the alkaline water from the pipe after a predetermined time (e.g. 5 to 30 minutes) and thereafter supplying strong acidic electrolysed water.

Further, the beer pipe washing/sterilisation method of the present invention may include a clearing step for removing strong acidic water which remains inside the beer pipe. For example, the clearing step may be carried out either by washing the inside of the beer pipe with tap water or by purging the beer pipe with carbon dioxide gas ($CO_2$ gas), as a supplementary step following the sterilisation step of introducing strong acidic electrolysed water from the water generator into the beer pipe. Particularly, it is more effective for removal of the strong acidic electrolysed water to purge the beer pipe with $CO_2$ gas and then to wash the inside thereof with tap water, following the sterilisation step of introducing strong acidic electrolysed water from the electrolysed functional water generator into the beer pipe.

BRIEF DESCRIPTION OF THE DRAWINGS

FIGS. 3 to 6 illustrate the processes of a preferred embodiment of the beer supply pipe washing/sterilisation method of the present invention.

DETAILED DESCRIPTION OF THE PREFERRED EMBODIMENTS

First of all, description is made of an electrolysed functional water generator employed in the beer pipe washing/sterilisation method of the present invention.

Figure 2:
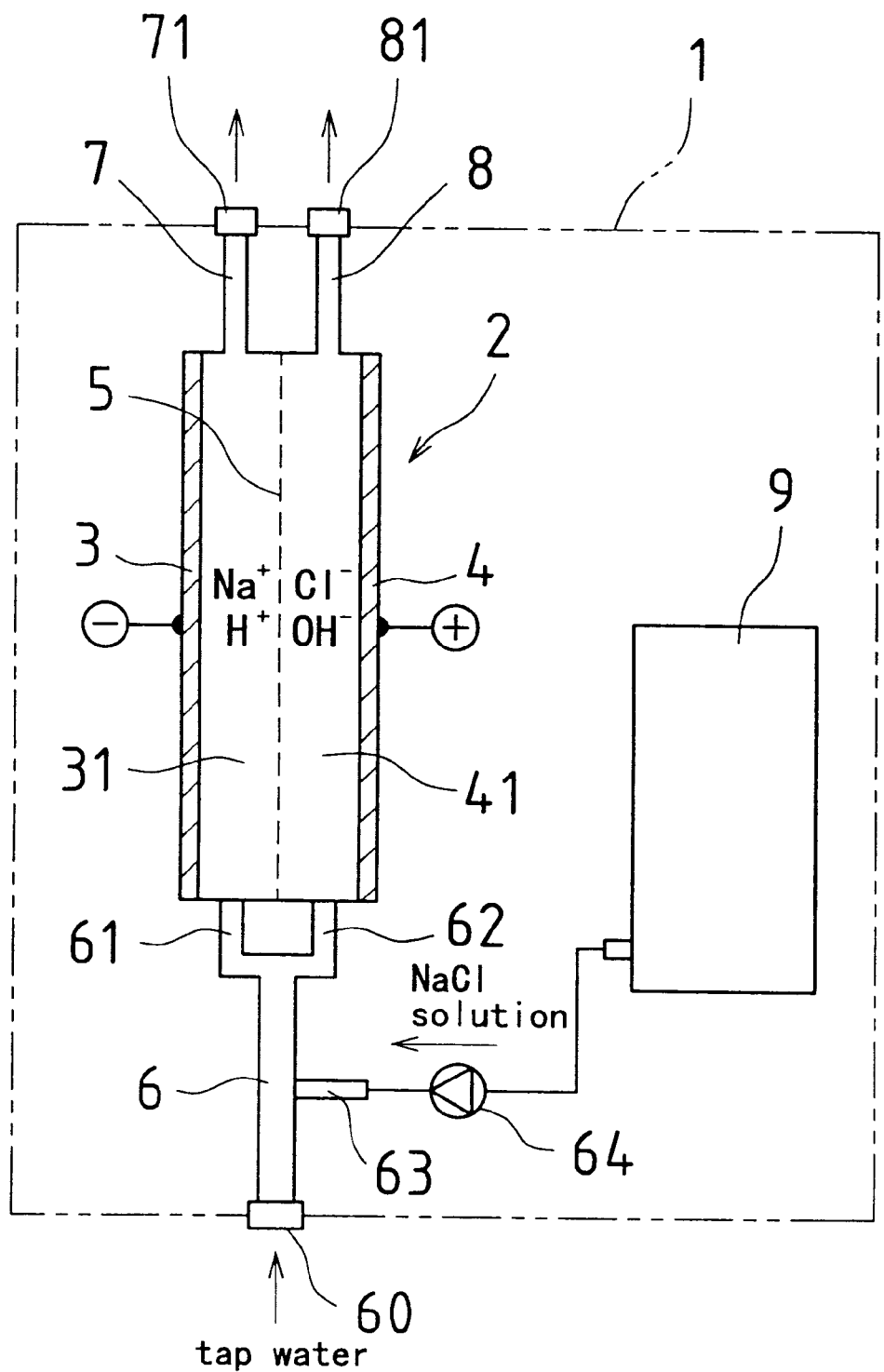
FIG. 2 is a schematic view of an electrolysed functional water generator employed in the beer supply pipe washing/sterilisation method of the present invention.

Referring to FIG. 2, an electrolysed functional water generator 1 includes an electrolytic cell 2 which contains an aqueous electrolyte solution with a trace of sodium chloride. The electrolytic cell 2 is equipped with a pair of opposing electrodes 3, 4 and divided into two compartments 31, 41 by a diaphragm 5 disposed in the middle of the electrodes 3, 4. Outlet pipes 7, 8 extend from the top of the compartments 31, 41 in a communicable manner, with the extreme ends of the pipes 7, 8 forming outlets 71, 81 of electrolysed waters.

A solution feed pipe 6 is laid below the electrolytic cell 2. The top end of the solution feed pipe 6 branches off in two solution passages 61, 62 which communicate with the bottom of the compartments 31, 41, respectively. The other end of the solution feed pipe 6 forms a water inlet 60 for feeding tap water. The solution feed pipe 6 receives, in the middle portion thereof, a NaCl feed pipe 63 for incorporating a sodium chloride solution (salt water) into the tap water. The NaCl feed pipe 63 is connected via a pump 64 to a tank 9 filled with a sodium chloride solution in a concentration of 20% or saturated salt solution.

In the above structure, each of the electrodes 3, 4 is an insoluble (corrosion-resistant) electrode such as a titanium substrate coated with a platinum group metal including platinum and indium. As the diaphragm 5, use can be made of a neutral porous membrane prepared by coating a polyester base with a fluoric material (e.g. polyvinylidene fluoride) or a chlorinated polyethylene, or a positive ion exchange membrane.

In the operation of the electrolysed functional water generator 1 of FIG. 2, the electrolytic cell 2 is filled with an aqueous electrolyte solution (sodium chloride content: 0.05 to 0.1% by weight) by supplying tap water from the water inlet 60 and adding a regulated amount of the sodium chloride solution to the tap water. Then, a direct voltage is applied to a pair of electrodes 3, 4 such that the electrode 4 is polarised into the anode. Thereby, the aqueous electrolyte solution is electrolysed to effect migration of positive ions (e.g. $Na^+$, $H^+$) from the anodic compartment 41 towards the cathodic compartment 31 as well as migration of negative ions (e.g. $Cl^-$, $OH^-$) from the cathodic compartment 31 towards the anodic compartment 41. As a result, strong alkaline electrolysed water is generated in the cathodic compartment 31, where $H^+$ ions discharge at the cathode to form hydrogen gas and the consumption of $H^+$ ions causes a relative increase of $OH^-$ ions. On the other hand, strong acidic electrolysed water is generated in the anodic compartment 41, where $OH^-$ ions discharge at the anode to form oxygen gas and the consumption of $OH^-$ ions causes a relative increase of $H^+$ ions. Besides, in the anodic compartment 41, $Cl^-$ ions discharge at the anode to form chlorine gas, which dissolves in water to give hypochlorous acid. In the electrolytic cell 2, the strong alkaline electrolysed water and strong acidic electrolysed water are carried upwardly by the influx of a fresh aqueous electrolyte solution and flow out through the outlet pipes 7, 8, respectively. In this way, the electrolysed functional water generator 1 of this embodiment can produce strong alkaline electrolysed water and strong acidic electrolysed water continuously.

Additionally, when a direct voltage of reversed polarity is applied to the electrodes 3, 4, the compartment 31 on the electrode 3 side is turned anodic to generate strong acidic electrolysed water, while the compartment 41 on the electrode 4 side is turned cathodic to generate strong alkaline electrolysed water.

As the electrolysed functional water generator, use can be made of ECO AQUA CLEAN JDS-101 (trade name; manufactured by JYONAN ELECTRIC INDUSTRIAL CO., LTD) of the following specification.

Strong Alkaline Electrolysed Water
  Generation rate: 1.0±0.1 l/min
  pH: 11.0 to 11.7
  ORP: −800 mV or lower
Strong Acidic Electrolysed Water
  Generation rate: 1.0±0.1 l/min
  pH: 2.3 to 2.7
  ORP: +1100 mV or greater Hereinafter, an embodiment of the beer supply pipe washing/sterilisation method is described with reference to the attached drawings.

Figure 3:
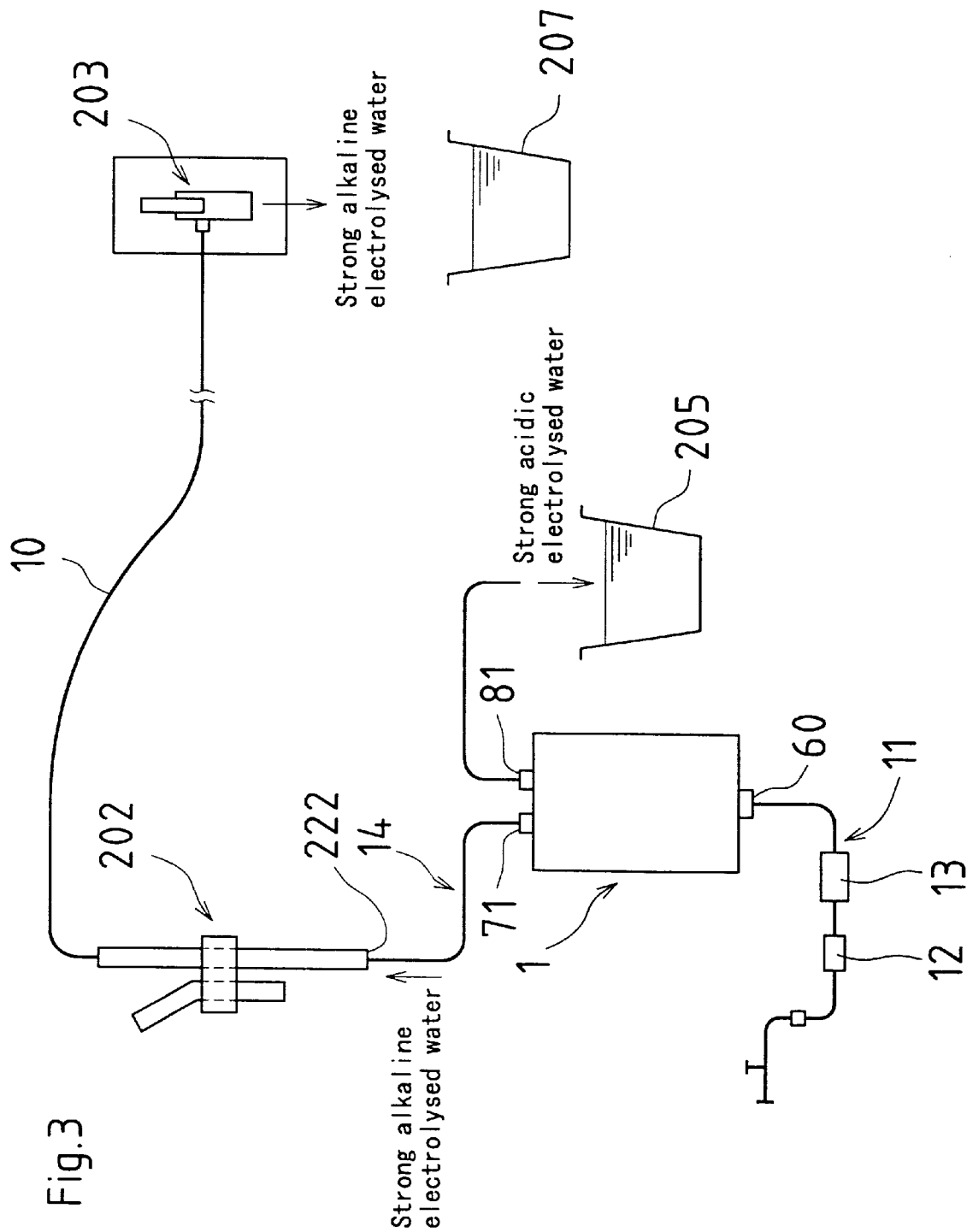

Referring to FIG. 3, a water pipe 11 is connected to the water inlet 60 of the electrolysed functional water generator 1. The water pipe 11 is equipped with a pressure reducing valve 12 and a prefilter 13.

The water generator 1 is disposed in the neighbourhood of a beer barrel 201 (shown in FIG. 1), and the outlet 71 of the water generator 1 is connected by a vinyl tube 14 to an inlet 222 of a connector 202 detachable with respect to the beer barrel 201. A tap 203 at the tip of the beer pipe 10 is held open. With these provisions made, the water generator 1 is started. The direct voltage applied to the electrodes 3, 4 has such a polarity as to turn the electrode 4 anodic. Consequently, strong alkaline electrolysed water is discharged from the outlet 71 leading to the connector 202 and flows through the beer pipe 10 at a flow rate of 1.0 l/min. This flow of alkaline water washes off the beer dregs deposited within the beer pipe 10.

At the same time, strong acidic electrolysed water is discharged from another outlet 81. This acidic water, which is unnecessary at the moment, is directed to a bucket 205 by a vinyl tube or the like and accumulated therein.

Figure 4:
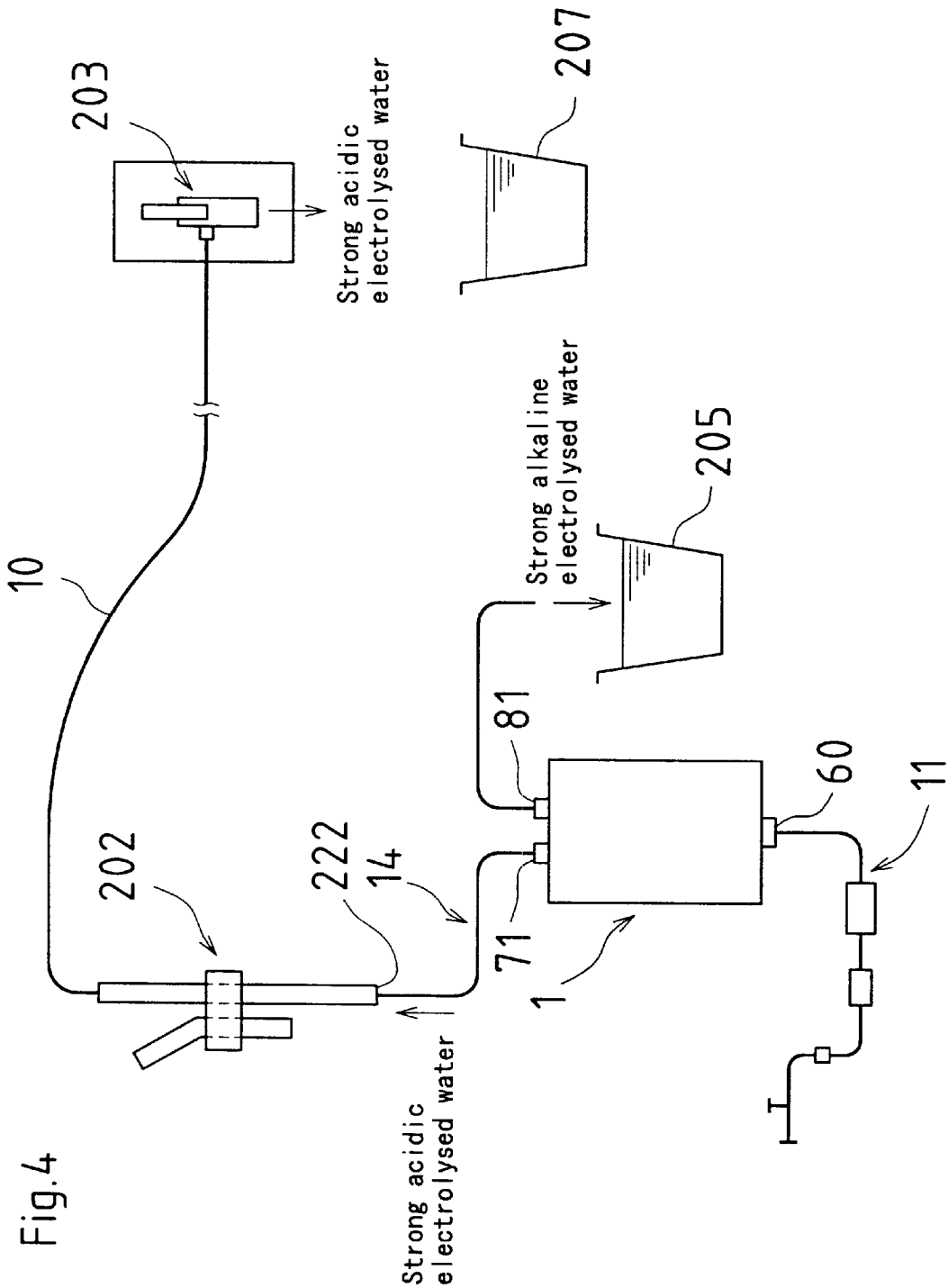

After 3 to 5 minutes of the above washing operation, the polarity of the direct voltage applied to the electrodes 3, 4 is reversed, so that strong acidic electrolysed water flows into the beer pipe 10 at a rate of 1.0 l/min, as shown in FIG. 4. This strong acidic electrolysed water can exterminate any bacteria or microorganisms existing in the beer pipe 10. It is said that the bacteria population in the beer pipe 10 is usually about $10^5$ to $10^7$ per milliliter. After strong acidic electrolysed water with a pH of 2.3 to 2.7 and an ORP of +1100 mV or greater is allowed to flow through the beer pipe 10 for 1 minute at a flow rate of 1.0 l/min, the bacteria population is diminished to 0. During the sterilisation step, by-produced strong alkaline water is unnecessary and directed into the bucket 205. The strong alkaline water neutralises with the accumulated strong acidic water, so that the bucket content is reduced to harmless water. Likewise, the strong alkaline water and strong acidic water discharged from the tap 203 can be collected in a bucket 207 for neutralisation.

Following the completion of the strong acidic water sterilisation, the connector 202 is disconnected from the water generator 1 and instead connected to a carbon dioxide cylinder 206 via a vinyl tube 15, as shown in FIG. 5. The beer pipe 10 is purged with carbon dioxide gas ($CO_2$ gas) to remove any residual strong acidic water completely. Thereafter, tap water is allowed to flow through the beer pipe 10 for washing the inner surface thereof. The tap water can be fed by switching the connector 202 to a water pipe 16, as shown in FIG. 6, or simply by deenergising the water generator 1 in the connection state illustrated in FIG. 3. With this treatment, the washing/sterilisation operation of the beer pipe 10 is completed.

Incidentally, the water generator 1 used in the above embodiment is driven by alternating the polarity of the direct voltage applied to the electrodes 3, 4. An additional advantage of this operation system is that the water generator 1 automatically removes (electrolyses) deposits or precipitates of calcium (Ca) and magnesium (Mg) which are derived from the tap water and deposited on the electrodes 3, 4 in the electrolytic cell 2. Due to the self-deposits removal ability, cleaning of the electrodes 3, 4 can be omitted.

In the above embodiment, the washing time (in which strong alkaline electrolysed water flows through the beer pipe 10) continues for 3 to 5 minutes, while the sterilisation time (in which strong acidic electrolysed water flows through the beer pipe 10) continues for 1 minute. The washing time and sterilisation time are not restricted as above but can be judiciously adjusted in accordance with the length of the beer pipe 10 and the degree of its contamination.

Following the sterilisation of the beer pipe 10, the above embodiment performs an acidic water clearing step which comprises purging the beer pipe 10 with $CO_2$ gas and washing the same with tap water. Actually, either one of these treatments will be sufficient. If the inside condition of the beer pipe 10 is acceptable after the sterilisation step, the purging/washing treatments may be substituted by an operation of introducing beer into the beer pipe 10 which still contains residual strong acidic electrolysed water and discarding the first flow of beer, as the final step of the washing/sterilisation method.

Now, description is directed to another embodiment of the beer pipe washing/sterilisation method of the present invention.

To begin with, the connector 202 is connected to the water generator 1 in the manner shown in FIG. 3. With a tap 203 at the tip of the beer pipe 10 being held open, the water generator 1 is driven to introduce strong alkaline electrolysed water into the beer pipe 10. When the strong alkaline water begins to flow out of the tap 203, the water generator 1 is stopped and the tap 203 is closed, whereby the beer pipe 10 is charged with the strong alkaline water. After this condition is kept for a while (e.g. about 5 minutes), the dregs deposited on the beer pipe 10 swell and peel off easily.

Thereafter, with the tap 203 at the end of the beer pipe 10 reopened, the water generator 1 is restarted to apply a direct voltage of reversed polarity to the electrodes 3, 4. Strong acidic electrolysed water is introduced into the beer pipe 10 for 5 minutes. Due to the influx of the strong acidic water, the strong alkaline water charged in the beer pipe 10 flushes out from the tap 203 together with the beer dregs, while the strong acidic water flowing through the beer pipe 10 kills the bacteria and microorganisms therein.

The washing/sterilisation steps are followed by the clearing step as shown in FIGS. 5 and 6 which comprises purging the beer pipe 10 with $CO_2$ gas and washing the same with tap water.

Additionally, after the strong alkaline water charged in the beer pipe 10 is drawn out, the beer pipe 10 may be left charged with the strong acidic water for a predetermined time (e.g. 1 to 5 minutes) for effective sterilisation.

Figure 7:
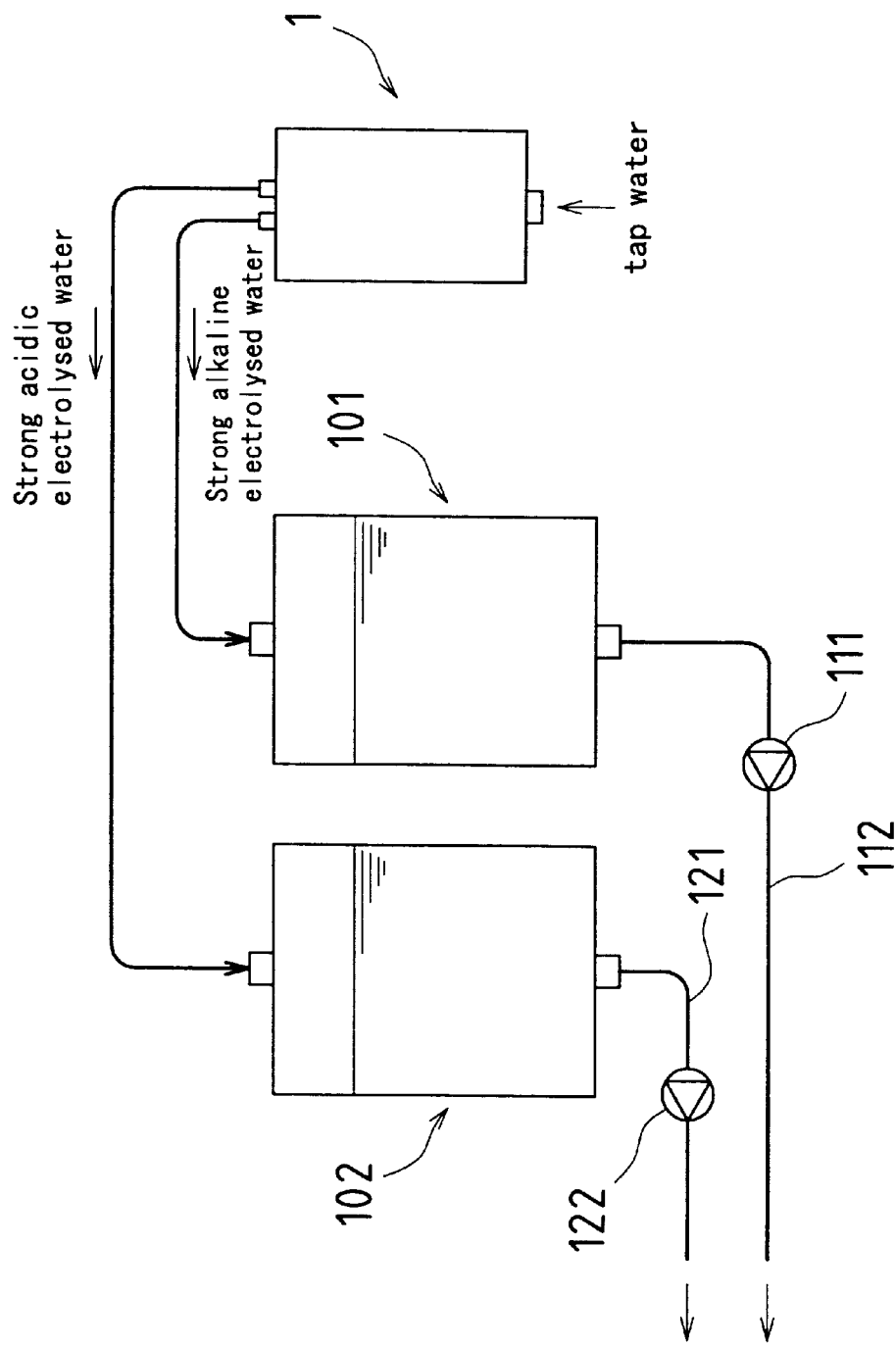
FIG. 7 illustrates another embodiment of the beer supply pipe washing/sterilisation method of the present invention.

In the above embodiments, the strong alkaline water and strong acidic water are supplied directly from the water generator 1 to the beer pipe 10. Alternatively, as shown in FIG. 7, the strong alkaline electrolysed water and strong acidic electrolysed water produced in the water generator 1 may be temporarily reserved in separate tanks 101, 102, respectively, from which each water is supplied to a beer pipe via pumps 111, 122 and vinyl tubes 112, 121.

The strong alkaline electrolysed water and strong acidic electrolysed water can be supplied from the tanks 101, 102 into the beer pipe in the same manner as in the above two embodiments. Namely, the strong alkaline water or the strong acidic water is allowed to flow through the beer pipe at a predetermined flow rate for the washing/sterilisation operation. Otherwise, the strong alkaline water is left charged in the beer pipe for a predetermined time, and, after the alkaline water is drawn out, the strong acidic water is supplied into the beer pipe.

Figure 1:
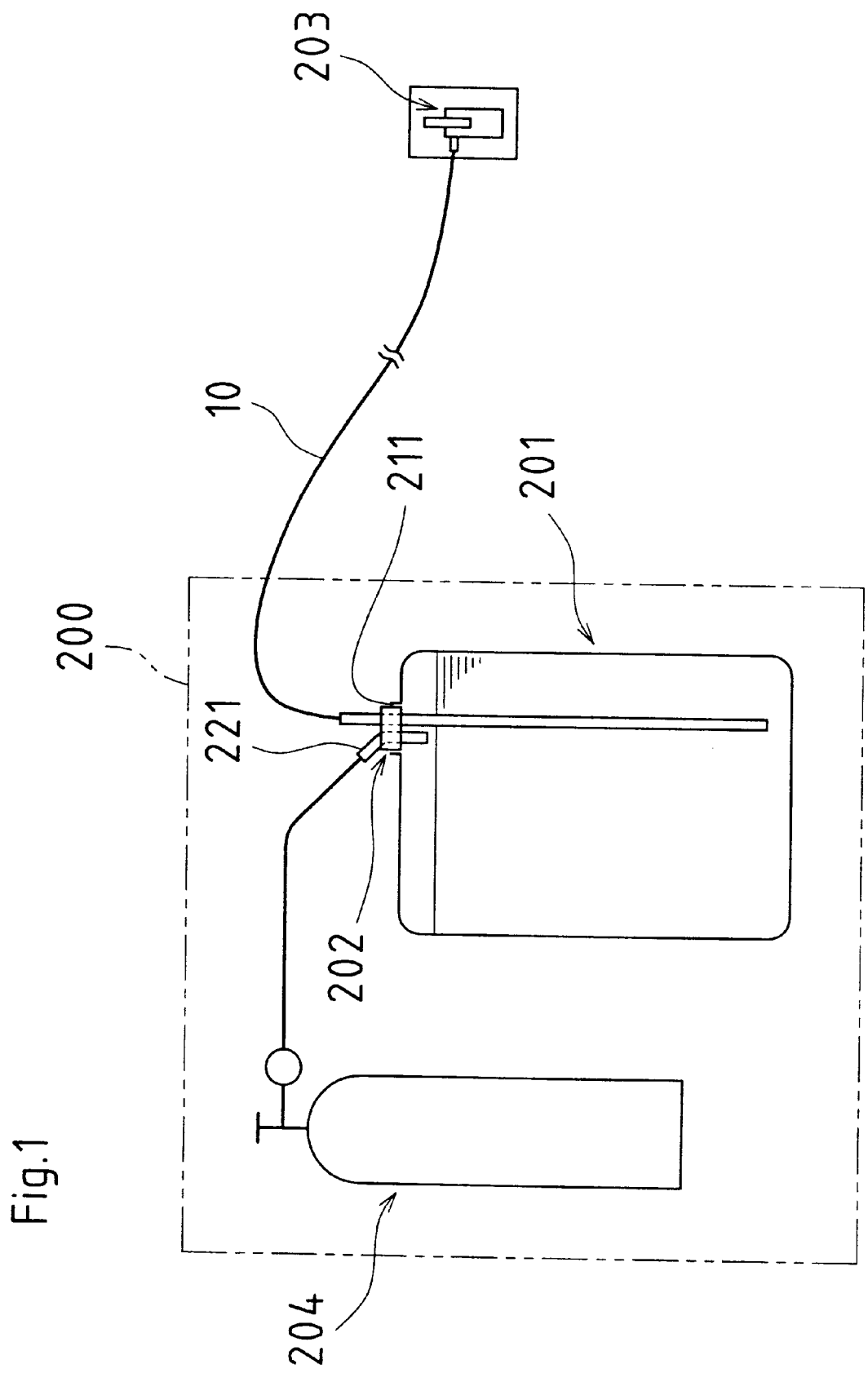
FIG. 1 is a schematic view of a draught beer supply system.

The above embodiments are directed to the washing and sterilisation of the beer pipe provided in the draught beer supply system shown in FIG. 1. However, the scope of the present invention should never be limited to the above embodiments. The present invention is further applicable to the washing and sterilisation of the pipe of a beer dispenser.

Although the embodiments in this specification deal with the washing and sterilisation of a beer pipe, the method of the present invention can be also modified for applications with respect to various pipes including vending machines for soft drinks, coffee, etc. and potting machines.

What is claimed is:

1. A method for washing and sterilising a beer supply pipe using water treated by an electrolysed functional water generator to remove impurities from an interior of the beer supply pipe, the method comprising:

producing a strong alkaline electrolysed water using the electrolysed functional water generator;

producing a strong acidic electrolysed water using the electrolysed functional water generator;

washing the interior of the beer supply pipe by introducing the strong alkaline electrolysed water into the interior of the beer supply pipe;

sterilising the interior of the beer supply pipe by introducing the strong acidic electrolysed water into the interior of the beer supply pipe, wherein the strong acidic electrolysed water removes the impurities from the interior of the beer supply pipe; and purging the interior of the beer supply pipe with carbon dioxide gas after the strong acidic electrolysed water is introduced into the interior of the beer supply pipe, wherein the strong alkaline electrolysed water has a hydrogen ion concentration (pH) in the range of 11.0 to 12.5 and an oxidation-reduction potential (ORP) of −650 mV or lower; and the strong acidic electrolysed water has a hydrogen ion concentration (pH) in the range of 1.5 to 3.0, an oxidation-reduction potential (ORP) of +1100 mV or greater and a chlorine concentration in the range of 10 to 50 ppm.

2. A method for washing and sterilising a beer supply pipe using water treated by an electrolysed functional water generator to remove impurities from an interior of the beer supply pipe, the method comprising:

producing a strong alkaline electrolysed water using the electrolysed functional water generator;

producing a strong acidic electrolysed water using the electrolysed functional water generator;

washing the interior of the beer supply pipe by introducing the strong alkaline electrolysed water into the interior of the beer supply pipe;

sterilising the interior of the beer supply pipe by introducing the strong acidic electrolysed water into the interior of the beer supply pipe, wherein the strong acidic electrolysed water removes the impurities from the interior of the beer supply pipe; and purging the interior of the beer supply pipe with carbon dioxide gas and washing the interior of the beer supply pipe with tap water after the step of introducing the strong acidic electrolysed water into the interior of the beer supply pipe, wherein the strong alkaline electrolysed water has a hydrogen ion concentration (pH) in the range of 11.0 to 12.5 and an oxidation-reduction potential (ORP) of −650 mV or lower; and the strong acidic electrolysed water has a hydrogen ion concentration (pH) in the range of 1.5 to 3.0, an oxidation-reduction potential (ORP) of +1100 mV or greater and a chlorine concentration in the range of 10 to 50 ppm.

3. A method for washing and sterilising a beer supply pipe using water treated by an electrolysed functional water generator to remove impurities from an interior of the beer supply pipe, the method comprising:

producing a strong alkaline electrolysed water using the electrolysed functional water generator;

producing a strong acidic electrolysed water using the electrolysed functional water generator;

washing the interior of the beer supply pipe by introducing the strong alkaline electrolysed water into the interior of the beer supply pipe;

sterilising the interior of the beer supply pipe by introducing the strong acidic electrolysed water into the interior of the beer supply pipe, wherein the strong acidic electrolysed water removes the impurities from the interior of the beer supply pipe; and purging the interior of the beer supply pipe with carbon dioxide gas after the strong acidic electrolysed water is introduced into the interior of the beer supply pipe.

4. The method for washing and sterilising a beer supply pipe as claimed in claim 3, wherein the strong alkaline electrolysed water has a hydrogen ion concentration (pH) in the range of 11.0 to 12.5 and an oxidation-reduction potential (ORP) of −650 mV or lower, and the strong acidic electrolysed water has a hydrogen ion concentration (pH) in the range of 1.5 to 3.0, an oxidation-reduction potential (ORP) of +1100 mV or greater and a chlorine concentration in the range of 10 to 50 ppm.

5. The method for washing and sterilising a beer supply pipe as claimed in claim 3, wherein the strong alkaline electrolysed water and the strong acidic electrolysed water flow through the interior of the beer supply pipe at a predetermined flow rate during the washing and sterilisation steps.

6. The method for washing and sterilising a beer supply pipe as claimed in claim 3, further comprising the steps of:
    maintaining the strong alkaline electrolysed water within the interior of the beer supply pipe for a predetermined period of time;
    withdrawing the strong alkaline electrolysed water from the interior of the beer supply pipe; and
    introducing the strong acidic electrolysed water into the interior of the beer supply pipe after the strong alkaline electrolysed water is withdrawn.

7. The method for washing and sterilising a beer supply pipe as claimed in claim 3, further comprises a step of washing the interior of the beer supply pipe with tap water after the strong acidic electrolysed water is introduced into the interior of the beer supply pipe.

8. The method for washing and sterilising a beer supply pipe as claimed in claim 3, further comprises the steps of purging the interior of the beer supply pipe with carbon dioxide gas and washing the interior of the beer supply pipe with tap water after the step of introducing the strong acidic electrolysed water into the interior of the beer supply pipe.

9. The method for washing and sterilising a beer supply pipe as claimed in claim 3, wherein the strong alkaline electrolysed water and the strong acidic electrolysed water are reserved in and supplied from separate tanks into the interior of the beer supply pipe.

10. A method for washing and sterilising a beer supply pipe using water treated by an electrolysed functional water generator to remove impurities from an interior of the beer supply pipe, the method comprising:
    producing a strong alkaline electrolysed water using the electrolysed functional water generator;
    producing a strong acidic electrolysed water using the electrolysed functional water generator;
    washing the interior of the beer supply pipe by introducing the strong alkaline electrolysed water into the interior of the beer supply pipe;
    sterilising the interior of the beer supply pipe by introducing the strong acidic electrolysed water into the interior of the beer supply pipe, wherein the strong acidic electrolysed water removes the impurities from the interior of the beer supply pipe; and
    purging the interior of the beer supply pipe with carbon dioxide gas, and washing the interior of the beer supply pipe with tap water after the step of introducing the strong acidic electrolysed water into the interior of the beer supply pipe.

11. The method for washing and sterilising a beer supply pipe as claimed in claim 10, wherein the strong alkaline electrolysed water has a hydrogen ion concentration (pH) in the range of 11.0 to 12.5 and an oxidation-reduction potential (ORP) of −650 mV or lower, and the strong acidic electrolysed water has a hydrogen ion concentration (pH) in the range of 1.5 to 3.0, an oxidation-reduction potential (ORP) of +1100 mV or greater and a chlorine concentration in the range of 10 to 50 ppm.

12. The method for washing and sterilising a beer supply pipe as claimed in claim 10, wherein the strong alkaline electrolysed water and the strong acidic electrolysed water flow through the interior of the beer supply pipe at a predetermined flow rate during the washing and sterilisation steps.

13. The method for washing and sterilising a beer supply pipe as claimed in claim 10, further comprising the steps of:
    maintaining the strong alkaline electrolysed water within the interior of the beer supply pipe for a predetermined period of time;
    withdrawing the strong alkaline electrolysed water from the interior of the beer supply pipe; and
    introducing the strong acidic electrolysed water into the interior of the beer supply pipe after the strong alkaline electrolysed water is withdrawn.

14. The method for washing and sterilising a beer supply pipe as claimed in claim 10, further comprises a step of washing the interior of the beer supply pipe with tap water after the strong acidic electrolysed water is introduced into the interior of the beer supply pipe.

15. The method for washing and sterilising a beer supply pipe as claimed in claim 10, further comprises the step of purging the interior of the beer supply pipe with carbon dioxide gas after the strong acidic electrolysed water is introduced into the interior of the beer supply pipe.

16. The method for washing and sterilising a beer supply pipe as claimed in claim 10, wherein the strong alkaline electrolysed water and the strong acidic electrolysed water are reserved in and supplied from separate tanks into the interior of the beer supply pipe.

* * * * *